United States Patent
Lawson et al.

[11] Patent Number: 6,030,404
[45] Date of Patent: Feb. 29, 2000

[54] SKIN PENETRATION APPARATUS INCLUDING MULTIPLE NEEDLE CONFIGURATION

[76] Inventors: Alexis A. Lawson; Michael Lawson, both of 2147 Altamont Rd., San Leandro, Calif. 94578

[21] Appl. No.: 09/178,188

[22] Filed: Oct. 23, 1998

Related U.S. Application Data

[63] Continuation-in-part of application No. 08/929,001, Sep. 6, 1997, abandoned.

[51] Int. Cl.$^7$ .................................................. A61B 17/34
[52] U.S. Cl. ............................................. 606/186
[58] Field of Search ................... 606/186, 223, 606/187, 188, 189; 604/272; 19/129 R

[56] References Cited

U.S. PATENT DOCUMENTS

| | | |
|---|---|---|
| 55,775 | 7/1866 | Klee . |
| 273,702 | 3/1883 | Bennett .................................. 606/186 |
| D. 355,255 | 2/1995 | Chou ..................................... D24/144 |
| 464,801 | 12/1891 | O'Reilly . |
| 693,554 | 2/1902 | Langstaff ............................... 606/186 |
| 3,086,530 | 4/1963 | Groom ................................... 606/186 |
| 3,193,908 | 7/1965 | White .................................... 19/129 R |
| 3,456,302 | 7/1969 | Nakagawa ................................ 19/234 |
| 4,031,783 | 6/1977 | Paul et al. ................................ 1/24 |
| 4,075,738 | 2/1978 | Egerer ................................... 19/234 |
| 4,159,659 | 7/1979 | Nightingale ............................ 30/362 |
| 4,771,660 | 9/1988 | Yacowitz ................................ 30/362 |
| 4,914,988 | 4/1990 | Chang .................................... 606/186 |
| 5,472,449 | 12/1995 | Chou ..................................... 606/186 |
| 5,586,473 | 12/1996 | Chou ..................................... 606/186 |
| 5,810,862 | 9/1998 | Pilmanis ................................ 606/186 |

FOREIGN PATENT DOCUMENTS

| | | |
|---|---|---|
| 584297 | 11/1924 | France . |
| 846 767 | 8/1952 | Germany . |
| 2 234 420 | 2/1991 | United Kingdom . |

OTHER PUBLICATIONS

U.S. application No. 08/929,001, Lawson, filed Sep. 6, 1997.

*Primary Examiner*—Michael Buiz
*Assistant Examiner*—(Jackie) Tan-Uyen T. Ho
*Attorney, Agent, or Firm*—Fenwick & West, LLP

[57] ABSTRACT

An array of elongated needles for penetrating skin is assembled in single or multiple tiers with the tips or points thereof substantially aligned along an axis or plane that is skewed in non-perpendicular orientation relative to the axes of elongation of the needles. The needles are rigidly confined in the assembly within a common base portion that extends to a boundary limit remote from the tips which is oriented along an axis or plane that is skewed in non-perpendicular orientation relative to axes of elongation of the needles. The axis or plane of the needle tips may be substantially parallel or non-parallel to the axis or plane of the boundary limit to promote selected resilient flexure characteristics of the needles in the portions thereof between the boundary limit of the base and the needle tips.

14 Claims, 2 Drawing Sheets

SKIN PENETRATION APPARATUS INCLUDING MULTIPLE NEEDLE CONFIGURATION

RELATED APPLICATION

This is a continuation in part application of application Ser. No. 08/929,001 entitled "Non-Electrical Tattooing Device With Interchangeable Multiple Needle Cartridges" filed on Sep. 6, 1997 by A. Lawson now abandoned.

FIELD OF THE INVENTION

This invention relates to multiple needle configurations particularly suitable for tattooing.

BACKGROUND OF THE INVENTION

Needles have long been used to penetrate the skin of an animal or human patient for delivering medicaments as in vaccinations, or dyes as in tattooing. Various schemes are known for holding a single needle or multiple needles to facilitate manipulation during use in penetrating the skin. Multiple needle configurations including an alignment of needles lying in a plane with the tips or points thereof aligned along a common axis are popularly used to penetrate the skin over relatively large areas that are to be tattooed. However, difficulties commonly arise in retaining multiple needles in alignment, or in a collated configuration, for simultaneous manipulation over an area of skin. An alignment axis of the tips or points of such multiple needles may be angled relative to the longitudinal axes of the needles to facilitate penetrating the skin at a non-perpendicular angle to the surface of the skin, thereby to penetrate the skin at such angle and facilitate lifting the skin in order to perfuse the skin thus lifted with tattooing dye. However, irregular characteristics of such aligned needles nearer the apex of axial alignment of the tips or points provide undesirable responsiveness when lifting skin penetrated by the multiple needles.

SUMMARY OF THE INVENTION

In accordance with the illustrated embodiments of the present invention, a plurality of needles are aligned or collated into a rigid assembly of contiguous needles with the tips or points thereof angled relative to the longitudinal axes of the needles, and with a boundary of the rigid assembly substantially aligned with the axis of alignment of the tips or points. Multiple needles assembled in this manner thus exhibit substantially uniform flexure resilience at all locations throughout the assembly as such assembly of needles is manually or mechanically manipulated to lift the skin simultaneously at multiple penetrations.

DETAILED DESCRIPTION OF THE INVENTION

Figure 1:
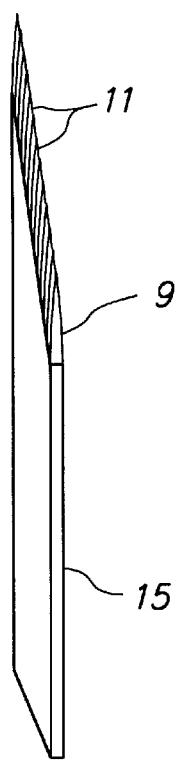
FIG. 1 is a perspective view of an assembly of multiple needles in a single-tier in accordance with one embodiment of the present invention.
Figure 2:
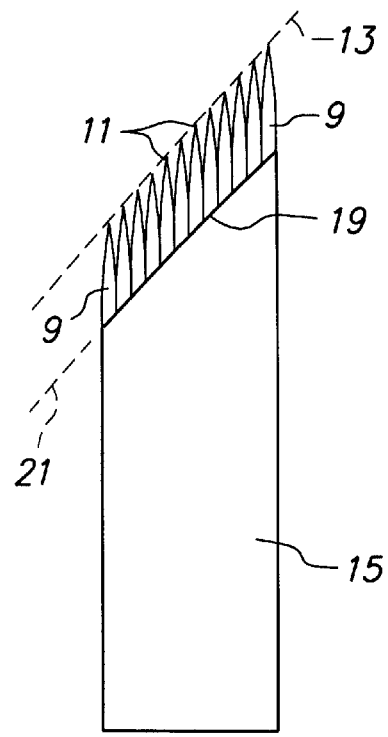
FIG. 2 is a plan view of the assembly of FIG. 1.
Figure 3:
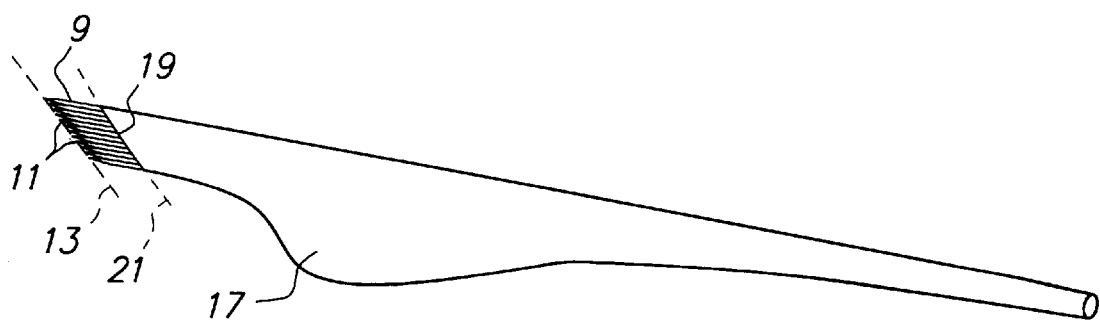
FIG. 3 is a plan view of a unitary structure including a single-tier needle assembly and holder in accordance with one embodiment of the present invention.

Referring now to the perspective view of FIG. 1 and the plan view of FIG. 2, there is shown a plurality of needles 9 arranged in parallel, contiguous array with the tips 11 thereof aligned along an axis 13 that is skewed relative to the longitudinal axes of the needles 9. A base portion 15 of the assembly holds the needles 9 in rigid formation, and may include solder, or epoxy or plastic molding, or a confining wrap of metallic or other sturdy tape, or the like, to form a substantially rigid assembly. As illustrated in FIG. 3, a unitary assembly may form the base portion 15 and a handle 17, for example, as a common casting of metal or plastic, or the like. The base portion 15, 17 includes a boundary limit 19 within which the needles 9 are rigidly constrained, and beyond which, toward the tips or points 11, the needles 9 are independently resiliently flexible. In accordance with one embodiment of the present invention, the boundary limit 19 of the base portion is substantially aligned 21 with the axis of alignment 13 of the tips or points 11 of the needles, which boundary limit 19 and alignment axis 13 are skewed from normal or perpendicular relationship to the parallel axes of the assembled needles 9 by an angle in the range from about 15 degrees to about 75 degrees. In this way, all needles 9 have substantially the same length beyond the base portion 15 for substantially uniform characteristics of resilient flexibility between the boundary 19 of the base portion 15 and the tips or points 11. In one embodiment of the invention, all needles 9 are formed in the same diameter of the same material such as stainless steel to provide the substantially uniform characteristics of resilient flexibility. In other embodiments, the boundary limit 19 may be skewed at one non-perpendicular angle, relative to the longitudinal axes of the needles 9 and the alignment axis 13 of the points 11 may be skewed at a second, more acute non-perpendicular angle than the one angle relative to the longitudinal axes of the needles 9. In this way, variations in resilient flexibility of the needles 9 beyond the boundary limit 19 of the base portion 15 may be altered over the array of needles of similar diameters, with resulting greater flexibility in needles 9 at and closest to the apex of the boundary limit 19 with the longitudinal axes of the needles 9. Also, the assembly of needles 9 may be formed from a billet-shaped piece of metal such as stainless steel with needle tips or points 11 etched or electro-eroded in conventional manner, or otherwise formed thereon to provide an assembly of contiguously-arrayed needles points 11 substantially aligned along an axis 13 that is skewed relative to a longitudinal axis of an outer edge of such billet at an angle from about 15 degrees to about 75 degrees. In one embodiment, the angle of alignment of the tips with the elongation axes of the needles may be about 45 degrees, and the angle of alignment of the boundary limit with such elongated axes may be substantially the same as, or different from, the angle of alignment of the tips. In embodiments where the angles are different, the resulting varied lengths of needles promote selected different resilient flexure characteristics of the needles at positions along the axis of alignment of the tips.

Figure 4:
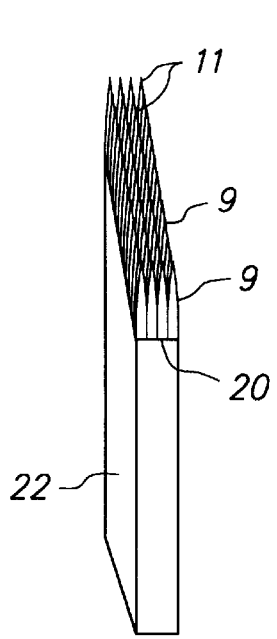
FIG. 4 is a perspective end view of an assembly of multiple needles in multiple tiers in accordance with an embodiment of the present invention.
Figure 5:
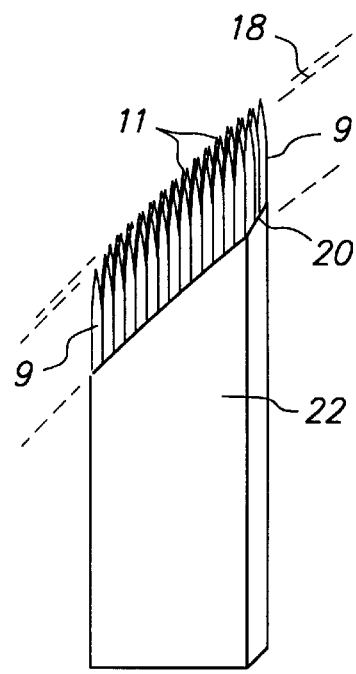
FIG. 5 is a perspective front view of the assembly of FIG. 4.
Figure 6:
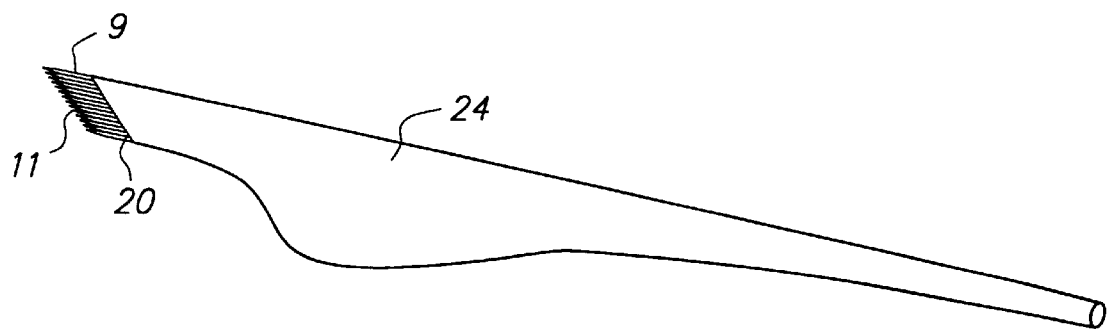
FIG. 6 is a plan view of a unitary structure including a multiple-tier needle assembly and holder in accordance with one embodiment of the present invention.

Referring now to the perspective views of FIGS. 4 and 5, and to the plan view of FIG. 6, there are shown assemblies of a plurality of needles 9 in multiple tiers arranged with all of the tips or points thereof 11 aligned in a plane 18 that is skewed relative to the longitudinal axes of the needles within a range of angles as described above. Additionally, the boundary limit 20 of the confining base portion 22 is substantially in a plane that is oriented substantially plane-parallel to the plane 18 of the tips or points 11 of the multiple tiers of needles 9. The confining base portion may be integrally formed with a handle 24, as illustrated in FIG. 6, as a common casting of metal or plastic, or the like, to the boundary limit 20 in relation to the tips or points 11 of the multiple tiers of needles 9, for the reasons as previously described with reference to the single tier of multiple needles 9 in the embodiments of FIGS. 1–3. Of course, in each of the embodiments of FIGS. 1 and 4, the assembly of single or multiple tiers of needles 9 may be confined in a base portion 15, 22, as previously described, to form a self-contained cartridge which may be secured within a collet-type knife handle of the type described and illustrated in the parent application cited above. Assemblies according to the illustrated embodiments of FIGS. 1–6 may be disposable after single-patient usage, or may be autoclavable or otherwise sterilizable for uses after each sterilization upon each of multiple patients.

What is claimed is:

1. An assembly of needles for penetrating the skin of a subject, comprising:

a plurality of elongated needles, each having a base portion and a tip, each of the needles being disposed in contiguous substantially parallel array in at least one tier with all of the tips thereof substantially aligned along a common axis at a first angle of skewed, non-perpendicular relationship to axes of elongation of the needles; and a base disposed about the base portion of the needles for rigidly constraining the plurality of needles within the assembly to a boundary limit along the elongated lengths of the needles remote from the tips thereof that is aligned along a common axis at a second angle of skewed, non-perpendicular relationship to the axes of elongation of the needles.

2. The assembly as in claim 1 wherein the first angle substantially equals the second angle.

3. The assembly as in claim 1 wherein the first angle is in the range from about 15 degrees to about 75 degrees.

4. The assembly as in claim 3 wherein the first and second angles are in the range from about 15 degrees to about 75 degrees.

5. The assembly as in claim 1 wherein the first angle is about 45 degrees.

6. The assembly as in claim 1 including a handle integrally formed with said base.

7. The assembly as in claim 6 which said handle is integrally formed with said base substantially to said boundary limit.

8. An assembly of needles for penetrating the skin of a subject, comprising:

a plurality of elongated needless each having a base portion and a tip, each of the needles being disposed in contiguous array in a plural number of tiers with all of the tips thereof substantially aligned within a plane at a first angle of skewed, non-perpendicular relationship to the axes of elongation of the needles; and a base disposed about the base portion of the needles for rigidly constraining the plurality of needles within the assembly to a boundary limit along the elongated lengths of the needles remote from the tips thereof that is aligned within a plane at a second angle of skewed, non-perpendicular relationship to the axes of elongation of the needles.

9. The assembly as in claim 8 wherein the first angle substantially equals the second angle.

10. The assembly as in claim 8 wherein the first angle is in the range from about 15 degrees to about 75 degrees.

11. The assembly as in claim 10 wherein the first and second angles are in the range from about 15 degrees to about 75 degrees.

12. The assembly as in claim 10 wherein the first angle is about 45 degrees.

13. The assembly as in claim 8 including a handle integrally formed with said base.

14. The assembly as in claim 13 in which said handle is integrally formed with said base substantially to said boundary limit.

\* \* \* \* \*